(12) United States Patent
Cochenour et al.

(10) Patent No.: US 7,887,571 B2
(45) Date of Patent: Feb. 15, 2011

(54) PATIENT ACTIVATED TEMPERATURE-CONTROLLED SURFACE

(76) Inventors: Cary B. Cochenour, 671 Adele Dr., North Huntingdon, PA (US) 15642; Craig G. Cochenour, 671 Adele Dr., North Huntingdon, PA (US) 15642

( * ) Notice: Subject to any disclaimer, the term of this patent is extended or adjusted under 35 U.S.C. 154(b) by 1012 days.

(21) Appl. No.: 10/785,555

(22) Filed: Feb. 24, 2004

(65) Prior Publication Data

US 2004/0172108 A1 Sep. 2, 2004

Related U.S. Application Data

(60) Provisional application No. 60/450,859, filed on Feb. 28, 2003.

(51) Int. Cl.
*A61F 7/00* (2006.01)
*A01K 29/00* (2006.01)
*A47C 21/04* (2006.01)

(52) U.S. Cl. .................. 607/96; 119/28.5; 219/217; 5/421

(58) Field of Classification Search ............... 5/284, 5/421–423, 520–521, 528, 530; 219/212, 219/217–218, 482, 526, 528; 165/200; 119/28.5; 607/96, 98, 108, 114; 297/180.11
See application file for complete search history.

(56) References Cited

U.S. PATENT DOCUMENTS

| 2,617,005 | A | * | 11/1952 | Jorgensen | .................. 219/508 |
|---|---|---|---|---|---|
| 3,041,441 | A | * | 6/1962 | Elbert et al. | ................. 392/435 |
| 4,332,214 | A | | 6/1982 | Cunningham | |
| 4,591,694 | A | | 5/1986 | Phillips | |
| 4,633,062 | A | * | 12/1986 | Nishida et al. | .............. 219/212 |
| 5,261,352 | A | | 11/1993 | Stammelman | |
| 5,303,485 | A | * | 4/1994 | Goldston et al. | .............. 36/137 |
| 5,516,189 | A | * | 5/1996 | Ligeras | .................. 297/180.11 |
| 6,084,209 | A | | 7/2000 | Reusche et al. | |
| 6,189,487 | B1 | * | 2/2001 | Owen et al. | ................. 119/28.5 |
| 6,237,531 | B1 | * | 5/2001 | Peeples et al. | ............. 119/28.5 |
| 7,134,715 | B1 | * | 11/2006 | Fristedt et al. | ......... 297/180.12 |
| 2004/0040946 | A1 | * | 3/2004 | Nation | ....................... 219/217 |
| 2004/0195227 | A1 | * | 10/2004 | Park | .......................... 219/217 |

FOREIGN PATENT DOCUMENTS

GB        2263396       *  7/1993

* cited by examiner

*Primary Examiner*—Lee S Cohen
(74) *Attorney, Agent, or Firm*—Craig G. Cochenour, Esq.; Buchanan Ingersoll & Rooney PC

(57) ABSTRACT

A patient activated temperature-controlled surface is disclosed. The patient activated temperature controlled surface includes a floor, a temperature source capable of supplying heat, cold, or both to the floor, and an actuator element for turning on and off the temperature source. The actuator element is activated and deactivated by the presence or absence, respectively, of the weight of the patient either directly or indirectly upon the actuator element. An animal bed is also disclosed. A method for providing comfort to a patient employing the patient activated temperature-controlled surface of this invention is also provided.

20 Claims, 2 Drawing Sheets

PATIENT ACTIVATED TEMPERATURE-CONTROLLED SURFACE

BENEFIT OF PRIOR PROVISIONAL PATENT APPLICATION

This utility patent application claims the benefit of co-pending U.S. Provisional Patent Application Serial No. 60/450,859, filed Feb. 28, 2003, entitled "Patient Activated Temperature-Controlled Surface" having the same named applicants as inventors, namely, Cary B. Cochenour and Craig G. Cochenour. The entire contents of U.S. Provisional Patent Application Serial No. 60/450,859 is incorporated by reference into this utility patent application.

BACKGROUND OF THE INVENTION

1. Field of the Invention

This invention relates to patient activated temperature-controlled surface. More particularly, this invention relates to a heated or cooled surface that is activated by the weight of the patient upon the patient's body contacting, directly or indirectly, the heated or cooled surface. The heated or cooled surfaces of the present invention may be a mat or bed of any shape suitable for use by a patient that is a human being, animal or creature.

2. Brief Description of the Background Art

Heated or cooled surfaces for patients, including pets or livestock or other animals, are known. For example, U.S. Pat. No. 4,591,694 provides a heated pet bed having a shell that is filled with a water layer. A heater is provided with a thermostat below an enclosure filled with water. The thermostat controls the temperature of the water layer above which the pet lays. U.S. Pat. No. 4,332,214 describes a heated bed for animals having an electric heater in a water compartment which surrounds a platform on which a pet rests.

Another example of a heated place for animals is set forth in U.S. Pat. No. 5,261,352. A heated space for cold blooded animals having a casting or molding of a rock-like formation is disclosed wherein a heating device is embedded within the material of the rock-like formation.

U.S. Pat. No. 6,084,209 provides a heating pad for animals consisting of a plastic housing and an electric heating element. The base of the housing contains conical supports upon which the heating element rests. The heating element is supported in the housing to provide air gaps above and below the heating element, allowing an even temperature throughout the housing. The heated pet bed set forth in U.S. Pat. No. 6,084,209 is concerned with preventing regions of localized heat on the top of the bed and also preventing unnecessary heating of the base. U.S. Pat. No. 6,189,487 provides a heated animal bed that includes a hollow blanket casing within which is disposed at least three layers of foam insulation material placed on top of another. A removable heating element is interposed between two adjacent layers of the foam material and supplies heat to the animal resting on the bed.

U.S. Pat. No. 6,237,531 describes a heated and cooled portable pet bed having an open structure with a hollow ring around its periphery. The ring traps air to provide a thermal barrier for the pet. A thermoelectric unit is mounted to its underside with appropriate ducting for air circulation so that either heating or cooling is provided to a sink which is integral with the platform of the bed.

In spite of this background art, there remains a very real and substantial need for a patient activated temperature-controlled surface as provided by the instant invention for providing either heat or cold to a surface only when the patient's body weight has activated either directly or indirectly the actuator element for turning on the temperature-controlled surface to which the heat or cold is supplied, such as for example a bed on which an animal may rest.

SUMMARY OF THE INVENTION

The present invention has met the above-described need. The patient activated temperature-controlled surface of the present invention provides for an efficient and economical temperature-controlled surface that is activated by the patient's weight, and thus is ideal for use with animals or creatures, such as for example but not limited to pets such as dogs, cats and snakes.

The present invention provides a patient activated temperature-controlled surface comprising a floor, a temperature source capable of supplying either heat or cold, or both, to the floor, and an actuator element that is capable of controlling the flow of an electrical current to the temperature source for turning on and off the temperature source, wherein the actuator element is activated and deactivated by the presence or absence of the weight of the patient. The actuator element is capable of allowing or preventing the flow of the electrical current to the temperature source. The actuator element is connected to a power source.

In a preferred embodiment of the present invention, the patient activated temperature-controlled surface, as described herein, includes wherein the temperature source is located in juxtaposition to the floor, and wherein the floor allows the heat or cold to pass from the temperature source through the floor, and wherein the actuator element is located in juxtaposition to the floor. More preferably, the present invention includes wherein the temperature source is located beneath the floor.

The patient activated temperature-controlled surface of the present invention includes wherein the actuator element provides an electrical bias. Preferably, the actuator element is a transistor, and most preferably the actuator element is a pressure-sensitive switch.

In another embodiment of the present invention, the patient activated temperature-controlled surface is a bed for accommodating the resting of the patient. In a preferred embodiment, the bed is surrounded by at least one wall. More preferably, the wall has at least one opening that allows for the ingress and egress of the patient in and out of the bed.

Another embodiment of the present invention provides a patient activated temperature-controlled surface, as described herein, including wherein the temperature source includes an adjustable thermostat.

The present invention provides an animal bed comprising a floor, a temperature source capable of supplying either heat or cold or both to the floor, and an actuator element that is capable of controlling the flow of an electrical current to the temperature source for turning on and off the temperature source, wherein the actuator element is activated and deactivated by the presence or absence, respectively, of the weight of the animal on the floor of the bed.

In another embodiment of the present invention, a method for providing comfort to a patient is set forth. This method comprises providing to a patient an activated temperature-controlled surface wherein the surface has a floor, a temperature source capable of supplying either heat or cold to the floor and an actuator element that is capable of turning on and off the temperature source, wherein the actuator element is activated and deactivated by the presence or absence, respectively, of the weight of the patient, and allowing the patient to contact the patient's body either directly or indirectly with the actuator element and turning on the temperature source for supplying heat or cold to the patient's body. The method further includes removing the patient's body from the actuator element for deactivating the actuator element and turning off the temperature source. Preferably the method includes allowing the weight of the patient to contact the floor of the temperature-controlled surface causing the floor to engage the temperature source and the temperature source to in turn engage the actuator element (i.e. indirect activation of the actuator element by patient's body weight) and thus allowing for the activation of the actuator element and turning on the temperature source. The method preferably includes wherein the patient's body weight is removed from the floor of the temperature-controlled surface and allowing the disengagement of the floor contacting the temperature source and in turn the disengagement of the temperature source contact with the actuator element (i.e. indirect deactivation of the actuator element by removal of the patient's body weight) and thus allowing for the deactivation of the actuator element and turning off of the temperature source.

Another embodiment of the method of the present invention provides including wherein the floor is a bed for accommodating the resting of the patient. Preferably, this method includes providing the bed surrounded by at least one wall. More preferably, this method includes providing the wall having at least one opening that allows for the ingress and egress of the patient in and out of the bed.

In yet another embodiment of the method of this invention, the method includes providing the temperature-controlled surface, as described herein, including wherein the temperature source has an adjustable thermostat.

The patient activated temperature-controlled surface and bed of the present invention will be more fully understood from the following descriptions of the invention, the drawings, and the claims appended hereto.

DETAILED DESCRIPTION OF THE INVENTION

Figure 1:
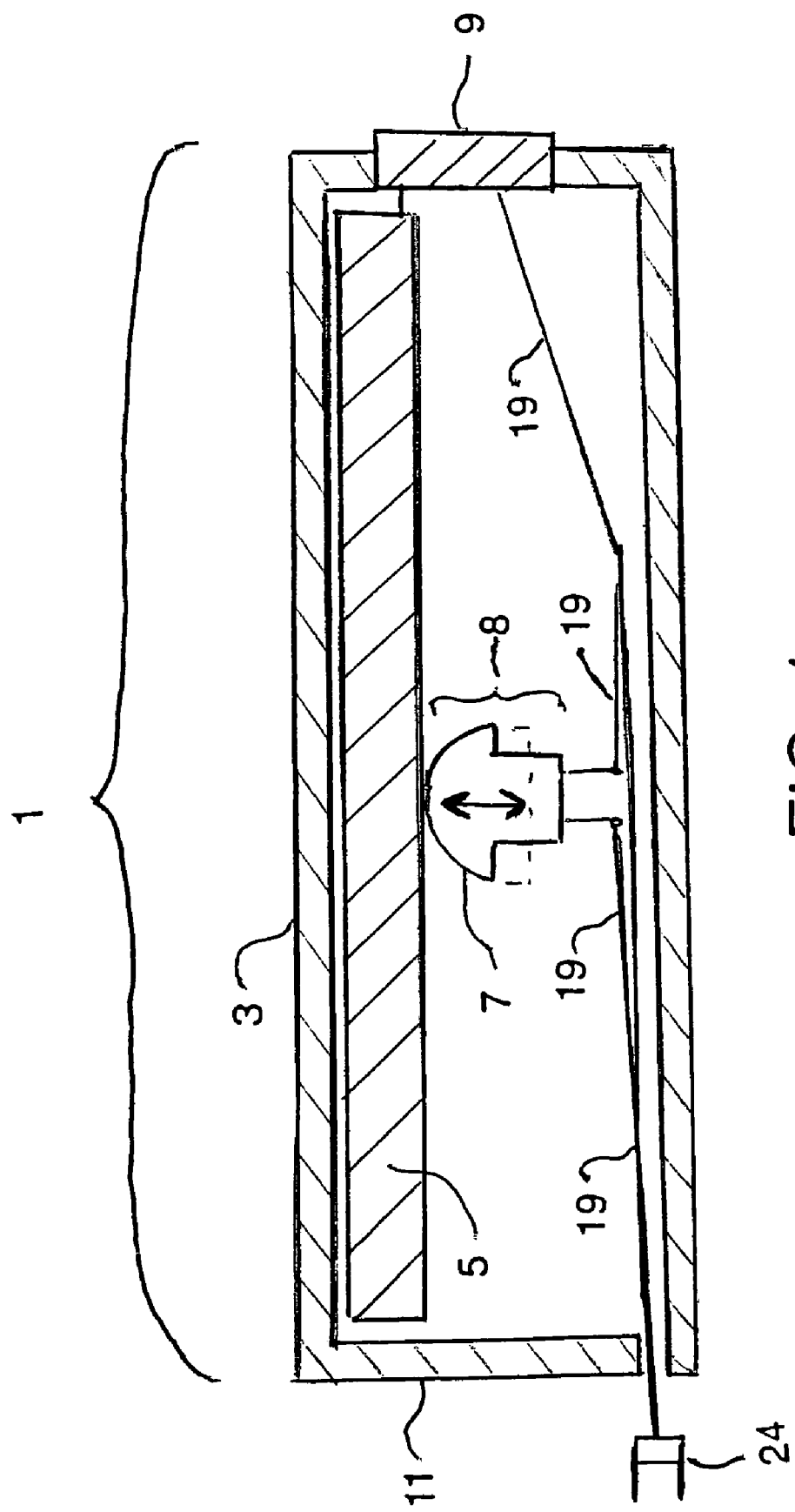
FIG. 1 is a sectional side view of a form of the patient activated temperature-controlled surface of the present invention.
Figure 2:
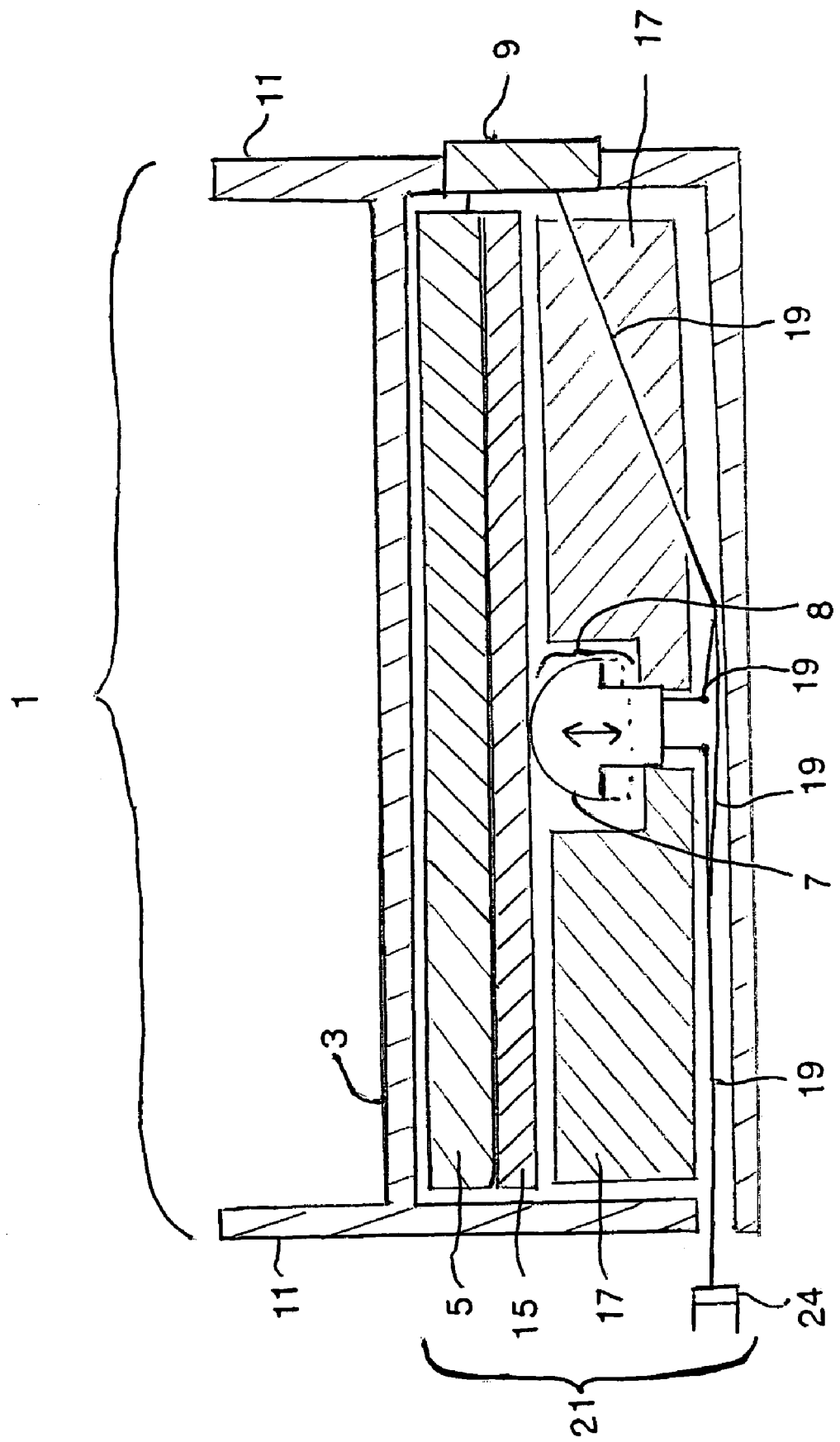
FIG. 2. is a sectional side view of a form of the animal bed of the present invention.

The present invention provides for a patient activated temperature-controlled surface for improving the comfort level of a patient. As used herein, the term "patient" means any animal or creature, warm or cold blooded, including such as for example but not limited to a human being, a dog, a cat, a horse, a cow, livestock, an elephant or a snake. The patient may or may not have a medical condition which may be ameliorated or relieved by heat or cold applied to the patient's body. Such medical conditions may include for example, arthritis, including but not limited to osteoarthritis and rheumatoid arthritis, and joint pain or arthralgia from over-activity of muscles and joints. FIGS. 1 and 2 illustrate preferred forms of the patient activated temperature-controlled surface and animal bed of the present invention.

In FIGS. 1 and 2, the patient activated temperature-controlled surface 1 of the present invention comprises a floor 3, a temperature source 5 that is capable of supplying either heat or cold or both to the floor 3, and an actuator element 7 that is capable of controlling the flow of an electrical current to the temperature source 5 for turning on and off the temperature source 5. The actuator element 7 is activated and deactivated by the presence or absence, respectively, of the weight of the patient. More preferably, the patient activated temperature-controlled surface 1 includes wherein the actuator element 7 is capable of allowing or preventing the flow of the electrical current to the temperature source 5. The patient activated temperature-controlled surface 1 of the present invention includes wherein the actuator element is connected to a power source (not shown in FIGS. 1 and 2). The actuator element may be activated directly by the patient's body weight or, preferably, the actuator element is indirectly activated by the patient's body weight. Preferably, the weight of the patient's body is allowed to contact the floor 3 of the temperature-controlled surface 1 causing the floor 3 to engage the temperature source 5 and the temperature source 5 to in turn engage the actuator element 7 (i.e. indirect activation of the actuator element 7 by patient's body weight) and thus allowing for the activation of the actuator element 7 and turning on the temperature source 5. Further, preferably, the patient's body weight may be removed from the floor 3 of the temperature-controlled surface 1 for allowing the disengagement of the floor 3 contacting the temperature source 5 and in turn the disengagement of the temperature source 5 contact with the actuator element 7 (i.e. indirect deactivation of the actuator element 7 by removal of the patient's body weight) and thus allowing for the deactivation of the actuator element 7 and turning off of the temperature source 5.

FIGS. 1 and 2 show a preferred embodiment of the patient activated temperature-controlled surface of the present invention wherein the temperature source 5 includes an adjustable thermostat 9. It is preferable that the thermostat provided with the present invention shall provide a heat setting or a cold setting such that the patient resting on the temperature controlled surface will not be harmed by either to hot or to cold of a temperature. This is particularly important for animals as they are not capable of adjusting the thermostat 9. Therefore, it is preferable that the thermostat 9 of the instant invention should have a limited heat or cold temperature range to limit the output of the temperature source 5.

FIGS. 1 and 2 show a preferred embodiment of the patient activated temperature-controlled surface of the present invention wherein the temperature source 5 is located in juxtaposition to the floor 3 and wherein the floor 3 allows for the heat or cold to pass from the temperature source 5 through the floor 3, and wherein the actuator element 7 is located in juxtaposition to the floor 3.

It will be appreciated by those skilled in the art that the temperature-controlled surface 1 must be made from a material, such as for example, foam or cloth, that shall allow for the heat or cold produced by the temperature source 5 to pass through the temperature-controlled surface 1 and, preferably, be felt by the patient's body resting on the floor 3.

In one embodiment, the patient activated temperature-controlled surface 1 of the present invention includes wherein the actuator element 7 provides an electrical bias.

In another embodiment of the present invention, the patient activated temperature-controlled surface 1 includes wherein the actuator element 7 is a transistor.

In yet another embodiment of the present invention, the patient activated temperature-controlled surface 1 includes wherein the actuator element 7 is a pressure-sensitive switch. More preferably, the pressure sensitive switch is a momentary switch 8 (as shown in FIGS. 1 and 2). The arrow shown on momentary switch 8 in FIGS. 1 and 2 indicates the up and down movement of the head of the momentary switch 8 that occurs when the body weight of the patient either directly or indirectly contacts the momentary switch 8 and when the patient's body weight is removed from contacting either directly or indirectly the momentary switch 8. The head of the momentary switch is pressed downward when the patients' body weight engages, either directly or indirectly, the momentary switch 8 and causes the momentary switch 8 to be activated for allowing the electrical current from the power source to flow to the temperature source 5 thus turning on the temperature source 5. When the patient's body weight is removed from contacting either directly or indirectly the head of the momentary switch 8, the head of the momentary switch 8 moves upward causing the momentary switch 8 to return to its deactivated position and preventing the flow of the electrical current to the temperature source 5 thus turning off the temperature source 5. It will be understood by those persons skilled in the art that the floor 3 of the present invention must be capable of being moved downward or capable of being deformed or depressed in order to establish contact of the patient's body weight, directly or indirectly, with the actuator element 7. The floor may be made from a material such as for example but not limited to cloth, vinyl, leather, plastic, polymeric materials, foil, or the like.

In a most preferable embodiment of this invention, FIGS. 1 and 2 show that the patient activated temperature-controlled surface 1 includes wherein the temperature source 5 is located beneath the floor 3.

FIGS. 1 and 2 show the patient activated temperature-controlled surface 1 wherein the floor 3 is a bed for accommodating the resting of the patient.

FIGS. 1 and 2 show the patient activated temperature-controlled surface 1 wherein the bed is surrounded by at least one wall 11. The animal bed of the present invention includes wherein the wall 11 of the patient activated temperature-controlled surface 1 includes at least one opening (not shown in FIGS. 1 and 2) that allows for the ingress and egress of the patient in and out of the bed.

FIG. 2 shows the animal bed of the present invention that optionally includes a first support 15 for supporting the temperature source 5 and an optional second support 17 for supporting the actuator element 7. The first support 15 and the second support 17 may be made of any material capable of supporting the weight of a patient, such as for example but not limited to wood, plastic, polymeric materials, and the like, and preferably the materials are non-flammable relative to the output of the temperature source 5 and the electrical connections 19 of the actuator element 7.

FIGS. 1 and 2 also show the electrical connection 19 of the actuator element 7 to an electrical source (not shown) and to the optional thermostat 9 of the temperature source 5.

The temperature source 5 is one that provides or generates heat (warm or hot temperatures) cold (cool or cold temperatures), or both, and may include for example, but not be limited to, a pad capable of providing a warm temperature in the case of heat production or a device for supplying a cool or cold temperature such as for example but not limited to a water cooler, electric fan, or refrigeration device, or the like. The pad capable of providing a warm sensation may be for example but not limited to a heating pad of a conventional design known by those skilled in the art and may have a heat control module or thermostat allowing the patient to select from one or more of a desired heat settings, such as for example, high, medium and low heat. Similarly, the device that provides a cold or cool sensation may be of conventional design as known by those skilled in the art and may have a cold or cool control module or thermostat allowing the patient to select one or more of a desired cold or cool settings. As used herein, the terms warm, hot, cool and cold have their ordinary meanings as will be appreciated by those skilled in the art.

It will be appreciated by those skilled in the art that one or more actuator elements 7 may be positioned in various places in juxtaposition and/or engagement with said temperature source 5 or the floor 3, or optionally the first support 15, and preferably within the inner compartment 21 of the bed around and under the floor 3, such that pressure or weight from a patient's body placed upon the floor 3 of the patient activated temperature-controlled surface 1 or the bed shall cause the floor 3 to push against the temperature source 5 (or directly upon the actuator element 7), and/or optionally the first support 15, and thus cause the temperature source 5, and/or the optional first support 15, to engage the actuator element 7 such that electrical current is allowed to flow through the electrical wires 19 and complete the electrical circuit to cause the temperature source 5 to be turned on. When weight or pressure is removed from floor 3 (i.e. when the patient is no longer resting on floor 3), the actuator element 7 will return to its original position and the flow of electrical current shall be prevented thus turning off the temperature source 5. The bed of the present invention conserves electricity when not in use, such that when the patient's body weight or pressure is removed from floor 3, the actuator element 7 prevents the flow of electrical power to the temperature source 5. The present invention may be applied to any surface of the present invention that the patient's body weight may come in contact with such as for example but not limited to the floor 3 of a mat or bed and/or one or more side walls 11 of a bed or container for a pet. The patient activated temperature-controlled surface or bed of the instant invention is particularly useful for a pet owner in that the pet owner's animal will automatically turn the temperature source 5 of the surface or bed on and off when the animal enters and exits, respectively, the surface or bed. The pet owner's electric utility usage will be lessened and thus conserved while the pet is not resting on the surface or in the bed of this invention. Further, this invention is convenient for the pet owner to use since the pet owner does not have to be bothered by constantly remembering to unplug the electrical cord 24 supplying the electrical current to the temperature source 5 of the patient activated temperature-controlled surface 1 or the bed from the electrical outlet when the animal decides to exit the temperature-controlled surface 1 or the bed. Similarly, the pet owner does not have to remember to plug the electrical cord into the electrical outlet when the pet desires to enter the temperature-controlled surface 1 or the bed of the instant invention. In other words, using the present invention eliminates the pet owner having to remember when to turn on and off the electrical supply as must be done with the known conventional heated or cooled pet beds. With the patient activated temperature-controlled surface and bed of the present invention, the pet owner shall be assured of their pet receiving either heat or cold to their pet's body when the pet lays on the floor 3, or optionally against a wall 11 of the temperature-controlled surface 1 or bed so equipped with the present invention, and be assured that the temperature-controlled surface 1 or bed is turned off when the animal exits, thus conserving valuable energy and lowering the pet owner's electric utility bill.

In another embodiment of the present invention, an animal bed is provided comprising a floor 3, a temperature source 5 capable of supplying either heat or cold or both to the floor 3, and an actuator element 7 that is capable of controlling the flow of an electrical current to the temperature source 5 for turning on and off the temperature source 5, wherein the actuator element 7 is activated and deactivated by the presence or absence, respectively, of the weight of the animal on the floor 3 of the bed.

In yet another embodiment of this invention, a method for providing comfort to a patient is provided comprising providing to a patient an activated temperature-controlled surface 1 having a floor 3, a temperature source 5 capable of supplying either heat or cold to the floor 3 and an actuator element 7 that is capable of turning on and off the temperature source 5, wherein the actuator element 7 is activated and deactivated by the presence or absence, respectively, of the weight of the patient, and allowing a patient to contact the patient's body with the floor 3 for supplying weight upon the floor 3 for activating the actuator element 7 and turning on the temperature source 5 for supplying heat or cold to the patient's body. This method further includes removing the patient's body from the floor 3 for allowing the actuator element 7 to deactivate and turning off the temperature source 5. Preferably, this method includes wherein the floor is a bed for accommodating the resting of the patient. More preferably, this method includes wherein the bed is surrounded by at least one wall 11. Most preferably, the method includes wherein the wall 11 has at least one opening (not shown in FIGS. 1 and 2) that allows for the ingress and egress of the patient in and out of the bed. In another embodiment, the method further includes providing the temperature source 5 with an adjustable thermostat 9.

Whereas particular embodiments of this invention have been described above for purposes of illustration, it will be evident to those persons skilled in the art that numerous variations of the details of the present invention may be made without departing from the invention as defined in the figures and the appended claims.

What is claimed is:

1. A patient activated temperature-controlled surface comprising a floor that moves in a down and an up direction, a temperature source that is in juxtaposition to and located beneath said movable floor and is surrounded by at least one wall, said temperature source capable of supplying either heat or cold, or both, to said floor, and one or more actuator elements that are capable of controlling the flow of an electrical non-direct current from an electric utility to said temperature source for turning on and off said temperature source, wherein said actuator element is (i) a separate and non-integral component in relationship to said temperature source, and (ii) is located beneath said floor and said temperature source and is unsecured to said wall, wherein said actuator element is activated and deactivated by the presence or absence of the weight of the patient upon said movable floor, said movable floor in engagement/disengagement with said temperature source, and said temperature source in engagement/disengagement with said actuator element, and an electrical cord for supplying said non-direct electrical current from said electric utility to said temperature source and wherein said actuator element is connected to said electrical cord.

2. The patient activated temperature-controlled surface of claim 1 wherein said actuator element is capable of allowing or preventing the flow of said non-direct electrical current to said temperature source.

3. The patient activated temperature-controlled surface of claim 1 wherein said electrical cord is connected to an electric utility supplying an alternating current.

4. The patient activated temperature-controlled surface of claim 1 wherein said movable floor allows said heat or cold to pass from said temperature source through said floor.

5. The patient activated temperature-controlled surface of claim 1 including wherein said actuator element provides an electrical bias.

6. The patient activated temperature-controlled surface of claim 1 wherein said actuator element is a transistor.

7. The patient activated temperature-controlled surface of claim 1 wherein said actuator element is a pressure-sensitive switch.

8. The patient activated temperature-controlled surface of claim 7 wherein said switch is a momentary switch.

9. The patient activated temperature-controlled surface of claim 1 further comprising a first support for supporting said temperature source, wherein said first support is located beneath said floor and said temperature source, and wherein said first support is located above said actuator element, wherein said moveable floor is in engagement/disengagement with said temperature source, and said temperature source is in engagement/disengagement with said first support, and wherein said first support is in engagement/disengagement with said actuator element, and wherein said first support is unattached to said wall.

10. The patient activated temperature-controlled surface of claim 1 wherein said movable floor is a bed for accommodating the resting of said patient.

11. The patient activated temperature-controlled surface of claim 10 wherein a portion of said wall extends above said movable floor.

12. The patient activated temperature-controlled surface of claim 11 including wherein said wall has at least one opening that allows for the ingress and egress of the patient in and out of said bed.

13. The patient activated temperature-controlled surface of claim 1 including wherein said temperature source includes an adjustable thermostat.

14. An animal bed comprising a floor that moves in a down and an up direction, a temperature source that is in juxtaposition to and located beneath said movable floor and is surrounded by at least one wall, said temperature source capable of supplying either heat or cold or both to said floor, and one or more actuator elements that are capable of controlling the flow of an electrical non-direct current from an electric utility to said temperature source for turning on and off said temperature source, wherein said actuator element (i) is a separate and non-integrated component in relationship to said temperature source, and (ii) is located beneath said floor and said temperature source and is unsecured to said wall, wherein said actuator element is activated and deactivated by the presence or absence of the weight of the animal on the movable floor, said movable floor in engagement/disengagement with said temperature source, and said temperature source in engagement/disengagement with said actuator element of said bed, and an electrical cord for supplying said non-direct electrical current from said electric utility to said temperature source and wherein said actuator element is connected to said electrical cord.

15. The animal bed of claim 14 further comprising a first support for supporting said temperature source, wherein said first support is located beneath said floor and said temperature source, and wherein said first support is located above said actuator element, wherein said moveable floor is in engagement/disengagement with said temperature source, and said temperature source is in engagement/disengagement with said first support, and wherein said first support is in engagement/disengagement with said actuator element, and wherein said first support is unattached to said wall.

16. A method of providing comfort to a patient comprising:
providing to a patient an activated temperature-controlled surface wherein said surface has a floor that moves in a down and an up direction, a temperature source that is in juxtaposition to and located beneath said movable floor and is surrounded by at least one wall, said temperature source capable of supplying either heat or cold or both to said floor, and one or more actuator elements that are capable of controlling the flow of an electrical non-direct current from an electric utility to said temperature source for turning on and off said temperature source, wherein said actuator element (i) is a separate and non-integrated component in relationship to said temperature source, and (ii) is located beneath said floor and said temperature source and is unsecured to said wall, wherein said actuator element is activated and deactivated by the presence or absence of the weight of the patient upon said movable floor, said movable floor in engagement/disengagement with said temperature source, and said temperature source in engagement/disengagement with said actuator element, and an electrical cord for supplying said non-direct electric current from said electric utility to said temperature source and wherein said actuator element is connected to said electrical cord; and allowing a patient to contact said patient's body with said movable floor of said surface for supplying weight upon said movable floor such that said movable floor engages said temperature source which in turn said temperature source thereby activating said actuator element and turning on said temperature source for supplying heat or cold to said patient's body.

17. The method of claim 16 including removing the patient's body from said movable floor of said surface for allowing said actuator element to deactivate and turning off said temperature source.

18. The method of claim 16 including wherein said movable floor is a bed for accommodating the resting of the patient.

19. The method of claim 18 including wherein a portion of said wall extends above said movable floor and including wherein said wall has at least one opening that allows for the ingress and egress of the patient in and out of said bed.

20. The method of claim 16 including providing said temperature source with an adjustable thermostat.

\* \* \* \* \*